US009068125B2

(12) United States Patent
Diehl et al.

(10) Patent No.: US 9,068,125 B2
(45) Date of Patent: Jun. 30, 2015

(54) PROCESS FOR THE RECOVERY OF PURE AROMATICS FROM HYDROCARBON FRACTIONS CONTAINING AROMATICS

(75) Inventors: Thomas Diehl, Frankfurt (DE); Helmut Gehrke, Bergkamen (DE); Baerbel Kolbe, Witten (DE); Dieter Wilken, Oelde (DE)

(73) Assignee: ThyssenKrupp Uhde GmbH, Dortmund (DE)

( * ) Notice: Subject to any disclaimer, the term of this patent is extended or adjusted under 35 U.S.C. 154(b) by 381 days.

(21) Appl. No.: 13/138,587

(22) PCT Filed: Feb. 18, 2010

(86) PCT No.: PCT/EP2010/001024
§ 371 (c)(1),
(2), (4) Date: Nov. 17, 2011

(87) PCT Pub. No.: WO2010/102712
PCT Pub. Date: Sep. 16, 2010

(65) Prior Publication Data
US 2012/0067776 A1    Mar. 22, 2012

(30) Foreign Application Priority Data

Mar. 11, 2009   (DE) .................... 10 2009 012 265

(51) Int. Cl.
*C10G 67/04* (2006.01)
*C10G 45/02* (2006.01)
(Continued)

(52) U.S. Cl.
CPC .. *C10G 7/08* (2013.01); *B01D 3/14* (2013.01); *B01D 3/141* (2013.01); *C07C 4/18* (2013.01);
(Continued)

(58) Field of Classification Search
CPC .......... C07C 4/18; C07C 15/02; C07C 15/06; B01D 3/14; B01D 3/141; C10G 2300/1096; C10G 2300/44; C10G 2400/30; C10G 45/58; C10G 47/02; C10G 47/22; C10G 7/08

USPC .......... 208/309, 311, 313, 321, 46, 133, 134, 208/141; 585/483, 486, 488
See application file for complete search history.

(56) References Cited

U.S. PATENT DOCUMENTS

| 3,197,523 A | 7/1965 | Michalko et al. |
| 3,304,340 A | 2/1967 | Noll |

(Continued)

FOREIGN PATENT DOCUMENTS

| DE | 1 568 940 A1 | 7/1970 |
| DE | 1 668 719 A1 | 3/1972 |
| DE | 198 49 651 A1 | 5/2000 |
| DE | 100 19 196 C1 | 9/2001 |
| EP | 0 792 928 A2 | 9/1997 |
| GB | 1166014 A | 10/1969 |
| GB | 1 174 279 A | 12/1969 |

OTHER PUBLICATIONS

Perry's Chemical Engineers Handbook, 2008, McGraw-Hill, 8th Ed., p. 13-15.*

*Primary Examiner* — Walter D Griffin
*Assistant Examiner* — Derek Mueller
(74) *Attorney, Agent, or Firm* — Marshall & Melhorn, LLC

(57) ABSTRACT

A process for the recovery of a pure aromatics-containing product is disclosed. This product is obtained by extractive distillation of a gasoline rich in aromatics, in which olefins, diolefins and polyolefins are separated, and this extractive distillation is followed by a hydrogenation of the recovered aromatics-rich, olefin-lean product stream, in which the alkylated aromatics, especially toluene and xylene, are dealkylated and the paraffinic dealkylation products further converted into methane so that a significant portion of hydrogen can be saved by carrying out the hydrogenation subsequent to the extractive distillation, as the aromatics mixture is then free of olefins and no hydrogen is required for an olefin hydrogenation, with extractive distillation and recovery of the extracting solvent taking place in one column. An apparatus for carrying out the process described is also disclosed. A column is preferably used for the extractive distillation which allows performing the extractive distillation with a solvent recycling system so that it is not required to provide an additional stripping column for removing the extracting solvent.

18 Claims, 3 Drawing Sheets

(51) Int. Cl.
*C10G 7/08* (2006.01)
*B01D 3/14* (2006.01)
*C07C 4/18* (2006.01)
*C07C 15/06* (2006.01)
*C10G 45/58* (2006.01)
*C10G 47/02* (2006.01)
*C10G 47/22* (2006.01)

(52) U.S. Cl.
CPC ............... *C07C 15/06* (2013.01); *C10G 45/58* (2013.01); *C10G 47/02* (2013.01); *C10G 47/22* (2013.01); *C10G 2300/1096* (2013.01); *C10G 2300/44* (2013.01); *C10G 2400/30* (2013.01)

(56) References Cited

U.S. PATENT DOCUMENTS

| | | | |
|---|---|---|---|
| 3,433,848 | A | 3/1969 | Devins et al. |
| 3,434,936 | A | 3/1969 | Luther et al. |
| 3,862,254 | A | 1/1975 | Eisenlohr et al. |
| 4,167,533 | A * | 9/1979 | Raymond ............ 585/251 |
| 4,215,231 | A * | 7/1980 | Raymond ............ 585/251 |
| 6,124,514 | A | 9/2000 | Emmrich et al. |
| 6,514,387 | B1 | 2/2003 | Emmrich et al. |

* cited by examiner

PROCESS FOR THE RECOVERY OF PURE AROMATICS FROM HYDROCARBON FRACTIONS CONTAINING AROMATICS

BACKGROUND OF THE INVENTION

The invention relates to a process for the recovery of pure aromatics from aromatics-containing hydrocarbon fractions and, in particular, from reformate gasoline, from fully hydrogenated pyrolysis gasoline, from coke-oven light oil refined under pressure or from mixtures thereof, with extractive distillation and recovery of the extracting solvent taking place in one column. The process according to the invention serves to provide aromatics and especially benzene, the alkylated benzene derivatives of the aromatics factions being converted by hydrodealkylation to give benzene or lower alkylated benzene derivatives. Depending on the design of the process high-purity products can be produced. By a novel process configuration it is possible to achieve a significant saving in expensive hydrogen used for the hydrodealkylation and in technical equipment. The invention also relates to an apparatus which serves to carry out this process.

Aromatics, particularly benzene, toluene and xylenes are important feedstocks used in the chemical industry, especially for the production of plastics and man-made fibres. In addition, aromatics are used to boost the octane number of Otto fuel. For the chemical industry application it is favourable to provide the required aromatics in the form of pure benzene as the demand for this chemical is especially high.

To recover benzene by hydrodealkylation, reformate gasoline, fully hydrogenated pyrolysis gasoline, coke-oven light oil refined under pressure or mixtures thereof may be used as hydrocarbon mixtures rich in aromatics. These feed products or mixtures thereof are hereinafter referred to as gasoline fractions. The used gasoline fractions contain major amounts of benzene derivatives, especially alkylaromatics. These can be converted by thermal or catalytic hydrogenation to give benzene, in which the alkyl substituents of the benzene are released and fully hydrogenated by reaction with hydrogen. This process of hydrodealkylation ("HDA") serves to obtain the required benzene. Apart from the required benzene, the alkyl substituents are obtained in the form of alkanes.

The reformate gasoline is a benzene rich in aromatics, which is produced by reforming and especially catalytic reforming of naphtha. During the reforming process, the alkanes and cycloalkanes contained in the petroleum or crude oil are subject to isomerizations, rearrangements, cyclizations, dehydrogenations and similar reactions. The aromatics-rich reformate gasoline obtained from catalytic reforming serves as an important feedstock in the recovery of aromatics.

The fully hydrogenated pyrolysis gasoline is a gasoline rich in aromatics which is obtained from steam cracking of hydrocarbons. Steam cracking of hydrocarbons mainly serves to generate lower olefins, especially ethene. Depending on the boiling range of the hydrocarbon mixture used for steam cracking, a large amount of a by-product rich in aromatics is obtained, the so-called pyrolysis gasoline, which, for further processing, is yet to be freed from unsaturated compounds and hetero-atoms (sulphur, nitrogen, oxygen) in various hydrogenation steps (selective hydrogenation, full hydrogenation). The product obtained from the hydrogenation steps is an aromatics-rich fraction which is referred to as a fully hydrogenated pyrolysis gasoline.

The coke-oven light oil refined under pressure is also a product rich in aromatics. Coke-oven crude light oil is obtained from the coking of coal. Similar to the pyrolysis gasoline, this coke-oven crude light oil still contains unsaturated compounds and hetero-atomic compounds apart from aromatics. Similar to the treatment of the pyrolysis gasoline, the coke-oven crude light oil is also hydrogenated to convert the unsaturated compounds as well as the hetero-atomic compounds. One of the products of this conversion is an aromatics-rich product which is free of unsaturated compounds and hetero-atomic compounds and can be used in a subsequent process. This aromatics-rich product is also referred to as coke-oven light oil refined under pressure.

The aromatics-rich hydrocarbon mixtures used may contain major amounts of non-aromatic compounds such as especially paraffins and naphthenes or olefins which are also hydrogenated in the hydrodealkylation giving alkane as hydrogenation product. If the hydrogenation is continued, methane is obtained from the cracking of alkanes. Depending on the stoichiometric amount of hydrogen used, the hydrodealkylation can also give lower alkylated benzene derivatives which have not been dealkylated completely to benzene.

The presence of large amounts of non-aromatic compounds in the feed stream to the hydrodealkylation requires an adequately large amount of hydrogen to carry out the reaction since hydrogen is not only required to dealkylate the alkylaromatics by hydrogenation to give benzene or lower alkylated benzene derivatives but also to decompose the longer chain non-aromatic compounds to short chain non-aromatic compounds. If the longer chain compounds are decomposed completely, methane is obtained. Therefore it is an aim of the invention to provide a process for the hydrodealkylation which minimises the use of hydrogen.

Apart from the required benzene, the hydrodealkylation also gives a mixture of short-chain paraffins or methane. The amount of gas generated by the dealkylation of aromatics cannot be influenced by the process according to the invention. It is, however, also the aim of this invention to reduce the amount of gas generated by the hydrogenation of the non-aromatic compounds also entrained in the feed stream.

To achieve these aims it is advantageous to first purify the hydrocarbon fraction to be submitted to hydrodealkylation in an extractive distillation. By carrying out the extractive distillation it is possible to separate a major part of the non-aromatic compounds already. The aromatics concentrate obtained from the extractive distillation can then be passed to a hydrodealkylation. As no hydrogen is consumed by the chain-shortening hydrogenation of the non-aromatic compounds which have already been removed from the starting mixture by an extractive distillation, a reduction in the amount of hydrogen consumed by the hydrodealkylation is achieved. In addition, the substance mixture contains lower portions of gaseous paraffins owing to the upstream installation of the extractive distillation after the hydrodealkylation. In this way it is possible to design the whole process for a lower gas flow rate which is of advantageous effect.

EP 792928 B1 describes a process for the recovery of pure aromatics from reformate gasoline. The teaching discloses a process in which, in a first process step, a reformate cut with aromatics of a selected carbon number or with aromatics of several selected carbon numbers $C_x$, $C_y$ is recovered from the reformate gasoline by fractionating distillation and the aromatics cut is hydrogenated selectively via a hydrogenating catalyst in a second process step, and, in a third process step, the selectively hydrogenated and aromatics-containing products from the second process step are then separated into aromatics and non-aromatic compounds by extractive distillation and/or liquid-liquid extraction. The hydrogenation conditions of the second process step are adjusted such that non-aromatic unsaturated hydrocarbons such as especially olefins, diolefins and triolefins are hydrogenated as well and conjugated diolefins and triolefins are hydrogenated as fully as possible.

DE 1568940 A1 describes a process for the separation of aromatics from hydrocarbon mixtures of any aromatics content, which may contain paraffins, cycloparaffins, olefins, diolefins and organic sulphur compounds as non-aromatic components, by extractive distillation. In the extractive distillation, especially N-substituted morpholines are used the substituents of which do not have more than seven C atoms. The aromatics fraction obtained can be submitted to a post-treatment, reference being made to a downstream sulphuric acid washing or a clay treatment. The impurities in the extracting agent, which especially consist of unsaturated hydrocarbons, gather in the bottom phase of the column and can be separated by bottom phase dehydrogenation and extractive distillation.

DE 10019196 C1 describes a process for the recovery of a high-purity aromatics product consisting of benzene and toluene or toluene and xylene from a close-boiling or azeotropic boiling intermediate product containing non-aromatic compounds and an apparatus for carrying out the process. The extractive distillation of non-aromatic compounds and the recovery of the extracting agent are performed in a single column consisting of a column main section comprising two parallel compartments, a rectifying section above the column main section, a stripping section below the column main section and a bottom with associated bottom heating. The starting gasoline is previously separated into at least two fractions by way of distillation, one of which is an aromatics fraction containing higher boiling non-aromatic compounds and a second is an aromatics fraction containing lower boiling non-aromatic compounds. The two fractions are introduced at separate feed points of the compartment of the column main section which is open at the upper and the lower end, the higher boiling aromatics fraction being introduced above the lower boiling aromatics fraction.

It is therefore the aim to provide a process in which an aromatics-rich starting gasoline is first depleted from the non-aromatic hydrocarbons by extractive distillation and the resulting aromatics concentrate is dealkylated by hydrogenation and converted into benzene or dealkylated aromatics as a product. After the hydrodealkylation the obtained aromatics concentrate should have such purity level that simple processing such as flashing, rectifying or both is enough to purify it. Depending on the design it should also be possible to add another hydrogenation treatment between the process steps of extractive distillation and hydrodealkylation in order to remove the residual olefins and polyunsaturated non-aromatic hydrocarbons.

Suitable feed gasolines for the extractive distillation, which have an adequately high content of aromatics, are, for instance, coke-oven light oil refined under pressure, fully hydrogenated pyrolysis gasoline or reformate gasoline which is usually obtained in large quantities in refineries. Depending on the starting gasoline it may be distilled into fractions before being used to increase the content in aromatics. The inventive apparatus should also be space-saving and facilitate reduced investment and operating costs.

BRIEF SUMMARY OF THE INVENTION

The invention achieves the aim by a process based on an aromatics-rich starting gasoline which is consecutively purified by extractive distillation first and finally dealkylated by hydrogenation and by extractive distillation and recovery of the extracting solvent in one column. Depending on the amounts of hydrogen and gasoline cut used, benzene is obtained or alkylated aromatics. From an aromatics-rich starting gasoline an aromatics concentrate rich in benzene or alkylated benzene derivatives is obtained, which, depending on the starting mixture, mainly contains toluene, xylenes and mesitylenes. The alkyl side chains are converted into alkanes during hydrogenation. Higher alkanes resulting from the hydrodealkylation of the side chains may fully be converted into methane as a result of the hydrogenation. The aromatics fractions obtained may, for example, be purified by rectification. Depending on the hydrogenation type and the purification steps the aromatics concentrate may be obtained with any purity level and dealkylation degree.

Carrying out the hydrodealkylation after the extractive distillation saves a significant amount of hydrogen, as the non-aromatic compounds which are contained in the starting gasoline are separated by the extractive distillation before the hydrodealkylation. As the gas amount of hydrogen as well as that of alkanes produced during the hydrogenation of the olefins is lower than in conventional processes, it is also possible to achieve a higher throughput of aromatics product. The inventive apparatus is also space-saving and facilitates reduced investment and operating costs.

Especially claimed is a process for the dealkylation of a hydrocarbon mixture rich in $C_7$ to $C_9$ aromatics, in which
the aromatics-rich starting hydrocarbon mixture is first submitted to an extractive distillation in which the aromatics-containing hydrocarbon mixture is distilled by means of a suitable extracting solvent and freed from it, obtaining a product flow significantly depleted from aromatic hydrocarbons and free of solvent as well as an aromatics concentrate significantly enriched in aromatic hydrocarbons and free of solvent, and
the solvent-free aromatics concentrate is passed to a reactor for hydrodealkylation after the extractive distillation, where it is reacted with hydrogen, giving a dealkylated aromatics stream as main product and a paraffinic hydrocarbon stream and a methane stream as by-products, and
the aromatic hydrocarbon stream is passed to a treatment unit, and
extractive distillation and recovery of the extracting solvent take place in one column.

The process according to the invention can be used to provide aromatics of the required alkylation degree in pure form. For the performance of the process it is also possible to interpose an additional hydrogenation step between the process steps of extractive distillation the hydrodealkylation in order to achieve the hydrogenation of the non-aromatic unsaturated hydrocarbons. This is required in particular if the portion of non-aromatic unsaturated compounds is still at an undesirably high level after the extractive distillation. Normally, however, this intermediate step is not required.

The process can be carried out with any apparatus that allows performing a hydrodealkylation after the extractive distillation. To implement the extractive distillation, a 1-column circuit as commonly known and being state-of-the-art is used. This is a special configuration of the extractive distillation which allows performing both an extractive distillation and a recovery of the extracting solvent in one column. This is space-saving and reduces the investment and operating costs.

The process according to the invention especially uses gasoline fractions the aromatics content of which is above 20 percent by weight. Preferably used are gasoline fractions the aromatics content of which is above 50 percent by weight. Ideal starting materials are gasoline fractions the aromatics content of which is above 80 percent by weight. Depending on the design, it is also possible to increase the aromatics content in the starting gasoline by pre-treatment steps (e.g. a pre-distillation).

Suitable gasoline fractions that may be used in the process according to the invention are, for example, fully hydrogenated pyrolysis gasolines. These are obtained as cracking products in the production of ethene and contain a high portion of aromatics. Further starting gasolines are catalytic reformate gasoline or coke-oven light oil refined under pressure. This may be a $C_7$ cut, a $C_{7,8}$ cut, a $C_{8,9}$ cut or a $C_{7-9}$ cut of these gasolines. These gasolines mostly contain an adequately high portion of aromatics due to the production process. Coke-oven light oil refined under pressure is especially suited for the recovery of pure benzene as its benzene content is high. Before the coke-oven light oil is used, it may be submitted to scrubbing or extraction processes in order to purify the gasoline fraction for the benzene production.

The process can be configured such that an aromatics-containing hydrocarbon mixture is directly used as feedstock and fed to the extractive distillation. The process, however, may also be configured such that the gasoline fraction undergoes a pre-treatment first. An optional pre-treatment step is, for instance, a rectification by which an aromatics cut of the required boiling point range is obtained. Also possible are extraction steps or scrubbing steps if the gasoline contains impurities, for example, or major amounts of paraffins. This may, for instance, be an extraction with a suitable solvent, water or an acid. This may, for example, be a scrubbing process with sulphuric acid for removing the olefins. It is also possible to perform a preceding extractive distillation to enrich an aromatics-lean starting gasoline with aromatics.

It is, for example, possible to implement an oxidation step to remove sulphur compounds or nitrogen compounds. It is also possible to implement an additional hydrogenation step to remove the sulphur compounds. If there is a high content of olefins or diolefins, it is also possible to carry out a pre-hydrogenation of the aromatics-containing starting mixture. This pre-hydrogenation will then be part of the process according to the invention. The pre-hydrogenation may also be used for desulphurisation.

The extractive distillation may be carried out with any solvent that allows separating aromatic hydrocarbons from a gasoline fraction. Especially suitable for this purpose are N-substituted solvents which contain 1 to 8 carbon atoms in the substituent. Especially suited for the extractive distillation is N-formyl morpholine. Also suited for the extractive distillation are, however, for example, N-methyl pyrrolidone, sulfolane, methyl sulfonales, dimethyl sulfoxide (DMSO), alkylene glycols or alkylated alkylene glycols. It is, of course, also possible to use solvent mixtures. The composition of the extractive solvent can be adapted to the process. It is also possible to add water to the extracting solvent, if required. Typical extractive distillation column temperatures and pressures range between 50 and 250° C. as well as 0.2 and 5 bar, resp.

The extractive distillation gives a fraction depleted from aromatics as well as the required aromatics concentrate. The extracting solvent is circulated in a loop and purified or filled up as required. The aromatics concentrate is then passed to the hydrodealkylation process step which normally follows the extractive distillation. In the case of some embodiments of the process according to the invention it may be advantageous to interpose a pre-hydrogenation between extractive distillation and hydrodealkylation. The choice of this process variant is left to the expert involved and is expressly part of the process according to the invention. For the hydrodealkylation process stage, both thermal and catalytic processes may be considered. Preferred are, however, thermal processes on account of the higher cost effectiveness.

A process for the production of aromatic compounds by thermal hydrodealkylation is described in DE 1668719 A1. A mixture of evaporated toluene and hydrogen is passed through an unpacked reaction coil, which is integrated into a heated heater, at a temperature of 760° C. within 5.4 seconds. The reaction parameters are controlled by keeping the temperature within confined limits during the reaction. The flow discharged from the dealkylation section is withdrawn and transferred as a liquid-gas mixture to a high-pressure separator for separating the liquid portions. These may then, for example, be regenerated in a distillation. The mentioned reaction gives a process yield for the hydrodealkylation of 88.5 percent benzene.

A process for the production of aromatic compounds by catalytic hydrodealkylation is described in U.S. Pat. No. 3,197,523A. The catalytic hydrodealkylation is carried out in a dealkylation section loaded with a catalyst, a reactor outlet flow being withdrawn at the outlet of the reactor and passed to a high-pressure separator. Here, a hydrogen-rich gas fraction and a liquid hydrocarbon fraction are obtained, the latter being transferred to a low-pressure separator, where lighter hydrocarbons are separated and another hydrocarbon fraction is obtained which is distilled giving the required benzene fraction. Typical pressures in the dealkylation section range between 20 and 100 bar, typical temperatures in the dealkylation zone range between 540 and 800° C.

In an advantageous commercial-scale embodiment the liquid starting mixture is evaporated with pre-heated hydrogen and a hydrogen-rich recycle gas and transferred to a pre-treatment reactor where the diolefins and triolefins contained in the mixture are hydrogenated and the sulphur compounds contained in the mixture, especially thiophene, are hydrogenated to give $H_2S$. The reaction mixture is then heated by a heating facility and passed through the actual dealkylation catalyst. The reactor outlet flow obtained is separated from the hydrogen-rich starting gas, the liquid fraction obtained is depressurised, in part recycled into the reactor if required and the aromatic product distilled. The reactor outlet flow is used for the generation of steam and heat. Depending on the purity degree the pure benzene obtained or the dealkylated aromatics are passed through fixed beds packed with clay material. Depending on the purity degree it is also possible to do without the pre-treatment stage.

The hydrodealkylation process stage is followed by the purification process step. Depending on the purity of the product obtained a so-called "flash" distillation may be used to minimise the demand for equipment. Also conceivable is, for example, a distillation or a freeze distillation stage.

The preferred product of the process according to the invention is pure benzene. Depending on the starting gasoline or the dealkylation degree it is also possible to obtain $C_7$ aromatics or a $C_{7/8}$ cut.

Owing to the more favourable process conditions and owing to the higher process yields, the thermal dealkylation is usually preferred, as it can be carried out more easily and leads to higher process yields if the process parameters are correct. This leads to the saving in hydrogen achieved by carrying out the hydrodealkylation after the extractive distillation. By this process variant it is also possible to achieve a higher product yield, as a lower amount of gaseous by-products are generated by the reduced portion of non-aromatic compounds after the extractive distillation. This causes a reduction in the amount of especially low-boiling hydrocarbons in the product, which leads to a lower gas load in the process and thus an improved feasibility and economic efficiency of the process.

Also claimed is an apparatus used to carry out the process according to the invention. Especially claimed is an apparatus for the dealkylation of a hydrocarbon mixture which is rich in aromatics, comprising a column for the extractive distillation, a reactor for hydrogenating the aromatics concentrate obtained, a purification unit for the treatment of the aromatic product obtained, the column for the extractive distillation, the hydrogenation reactor and the purification unit being arranged such that an extractive distillation of aromatic hydrocarbons from a hydrocarbonaceous mixture, a separation of extracting solvent from the aromatic product flow, a hydrodealkylation of aromatics for obtaining a dealkylated aromatic product and a purification of the aromatic product obtained are carried out one after the other in direction of the process flow, and the apparatus comprises a column which facilitates an extractive distillation and the recovery of the extracting solvent in one column.

Various optional design types may be used for the mentioned apparatuses. These may include apparatuses required for or supporting the distillation as there are reboilers, heating apparatuses or pumps for maintaining a vacuum. Such an arrangement is described in EP 792 928 B1, for example.

The extractive distillation process step is carried out in a column which permits to perform the extractive distillation and the separation of the extracting solvent in one column. An example for such column allowing an extractive distillation and a separation of the extracting solvent from the aromatics-containing product fraction in one column is described in DE 19849651 A1. Here, the extracting solvent is circulated in a loop. The column is provided with heaters for the extracting solvent in order to maintain the distillation heat. It may also be provided with apparatuses for heating the flow of aromatics, here to be mentioned are, for example, reboilers in the bottom of the column. The column permitting an extractive distillation in one column facility may, however, be of any desired type.

Especially claimed is an apparatus for the dealkylation of a hydrocarbon mixture rich in aromatics, comprising a column which allows to carry out an extractive distillation and the recovery of the extracting solvent in one single column, this column including a stripping section below the column main section, a rectifying section above the column main section, a main column section consisting of two parallel compartments and a column bottom with associated bottom heating, and the one compartment of the main column section being open towards the interior space of the column at the upper and at the lower end, and the other compartment being closed towards the interior space of the column at the upper end and open towards the interior space of the column at the lower end; all compartments containing internals for an improved mass transfer and above the internals of the compartment which is closed towards the interior space at the upper end and open towards the interior space of the column at the lower end, devices being installed which ensure the vaporous outlet flow of an extracting-solvent-free product and the reflux of a liquefied partial product flow.

To perform the hydrodealkylation, apparatuses can be used that allow to perform a hydrodealkylation in a state-of-the-art manner, recycling of the excessive hydrogenation hydrogen and purification of the pure benzene flow or of the pure aromatics fraction and also, if required, subsequent processing of the obtained methane flow. These include, for example, packed columns, evaporators, distilling towers, hydrogenation reactors with catalyst inventories or diffusion separators. The apparatus for the performance of the hydrodealkylation may, however, be of any desired type but suitable for the hydrodeakylation of a flow of aromatics which is typically obtained in the extractive distillation of an aromatics-containing hydrocarbon mixture.

To pre-treat the starting gasoline and the aromatics-containing starting mixture, it is necessary to provide apparatuses to carry out these process steps. Pre-treatment may, for example, require the provision of distilling columns for a fractional distillation, extraction towers or freeze distillation facilities. If such apparatuses are used in the process according to the invention, they are expressly part of the process according to the invention. Included in the process according to the invention are also process steps for the purification of the aromatics-containing product after the hydrodealkylation. For this purpose distilling column for a fractional distillation, flash distilling units, fixed beds with clay packing or freeze distillation stages can be used.

Finally all apparatus components may include devices which are required to maintain operation of the extractive distillation and the hydrodealkylation of aromatics. These are, for instance, compressors, turbines, pumps and valves. These are, of course, also apparatuses that serve to maintain the necessary operating temperatures, to be mentioned here, for example, are heaters, burners, heat exchangers or coolers. These finally also include the required control instruments such as thermostats or controllers.

The process according to the invention and the apparatus according to the invention involve the advantage that the apparatus for the production of pure aromatics-containing products can be arranged in a conventional mode, the production requiring a significantly lower amount of hydrogen than in the conventional processes. By this process it is also possible to achieve a considerably higher throughput than in conventional arrangements for the production of pure aromatics. The described arrangement is especially suited for the production of pure benzene but can also be used for the production of alkylated fractions rich in aromatics such as toluene.

The configuration of a process for the production of aromatics-containing hydrocarbon mixtures according to the invention is illustrated by means of an example describing the procedure and the composition of the starting mixture and of the aromatics concentrate after the extractive distillation.

Example

An aromatics-containing hydrocarbon mixture of fully hydrogenated pyrolysis gasoline with an aromatics content of 86 percent in mass is submitted to an extractive distillation for which the apparatus according to DE 19849651 A1 is used as well as N-formyl morpholine as extracting solvent. The composition of the aromatics-containing starting mixture before and after the extractive distillation is specified in Table 1. The components were determined by gas chromatographic analysis of the fractions. The extractive distillation is followed by a hydrodealkylation in which the mixture obtained from the extractive distillation is converted by means of hydrogen in a hydrodealkylation unit. The product obtained is a dealkylated and aromatics-containing product.

If the starting mixture according to the example is submitted to a hydrodealkylation, 38.7 kg hydrogen are required for 1000 kg starting mixture each and 718 kg benzene are obtained. The gas load in the reactor outlet is 636 Nm$^3$ (not taking into consideration a necessary hydrogen excess). If, however, the aromatics concentrate obtained from the extractive distillation is submitted to a hydrodealkylation, 24.4 kg hydrogen are required for 1000 kg aromatics concentrate each and 825 kg benzene are obtained. The gas load in the reactor outlet is 507 Nm$^3$ (not taking into consideration a necessary hydrogen excess). This example demonstrates the advantageous embodiment of the invention.

The configuration of a process flow for the production of dealkylated aromatics-containing hydrocarbon mixtures in accordance with the invention is described in more detail by means of three drawings, the process according to the invention not being limited to these embodiments.

DETAILED DESCRIPTION OF THE INVENTION

Figure 1:
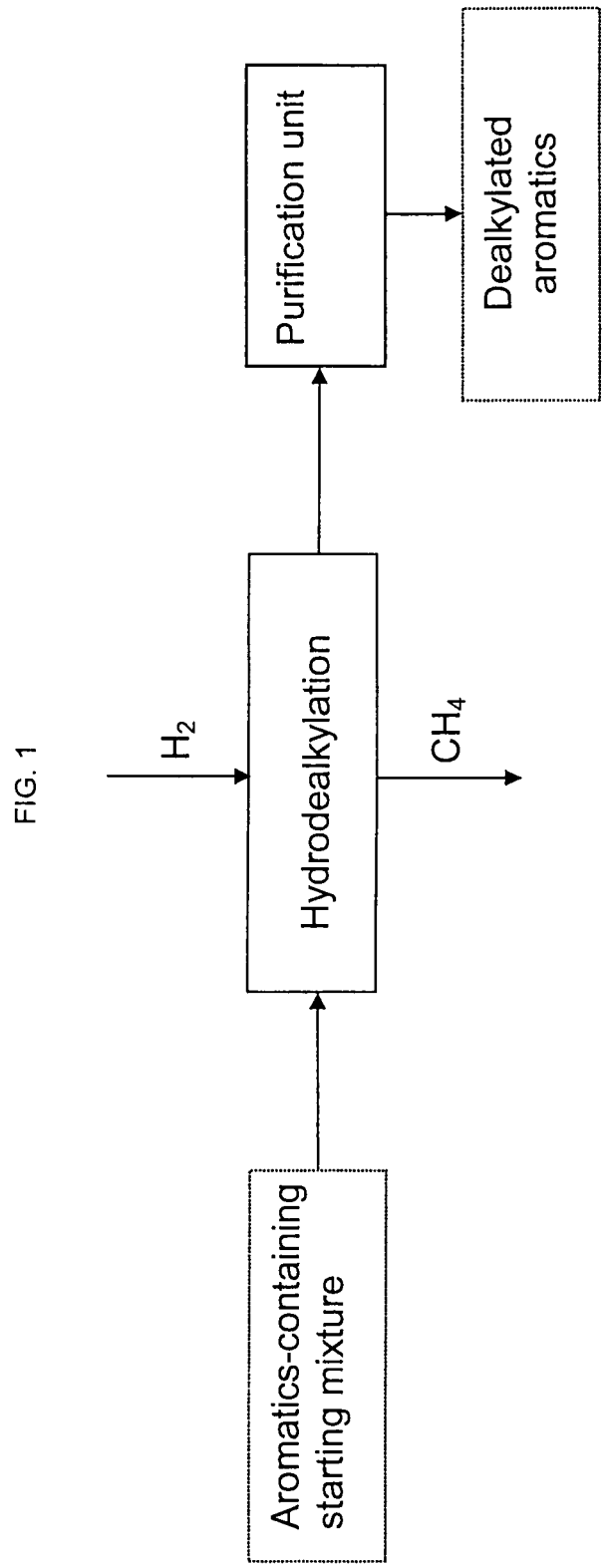
FIG. 1 shows a process flow diagram of a hydrodealkylation.

FIG. 1 shows a process flow diagram of a hydrodealkylation as arranged according to the state of the art. The aromatics-containing starting mixture is transferred to a hydrodealkylation unit. To carry out the reaction, this reaction stage is further supplied with hydrogen. In the hydrodealkylation, methane is obtained from the hydrogenation of the alkyl side chains. A product flow of dealkylated aromatics is obtained which is treated in a purification unit. A pure product of dealkylated aromatics is obtained. Olefins which are contained in the aromatics concentrate are also hydrogenated.

Figure 2:
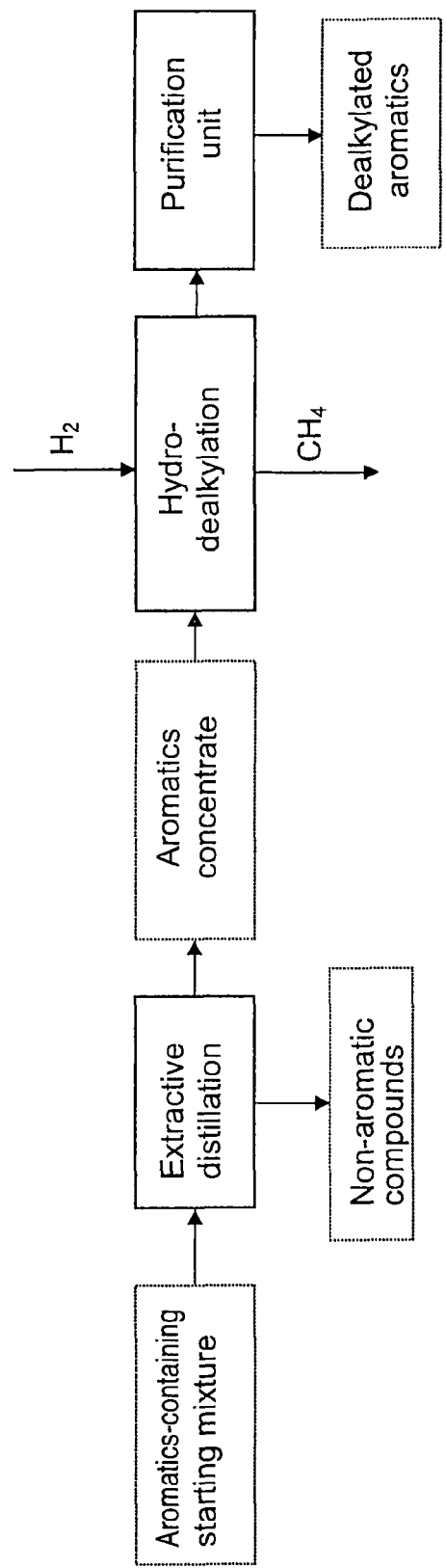
FIG. 2 shows a process flow diagram of an embodiment of the present invention.

FIG. 2 shows a process flow diagram of the process according to the invention. An aromatics-containing starting mixture of hydrocarbons is fed into an extractive distillation. Obtained is a hydrocarbon flow depleted from aromatics and a hydrocarbon flow enriched in aromatics. The hydrocarbon flow enriched in aromatics is passed as aromatics concentrate to the hydrodealkylation process unit. To carry out the reaction, this reaction stage is further supplied with hydrogen. In the hydrodealkylation methane is obtained from the hydrogenation of the alkyl side chains. A product flow of dealkylated aromatics is obtained which is treated in a purification unit. A pure product of dealkylated aromatics is obtained.

Figure 3:
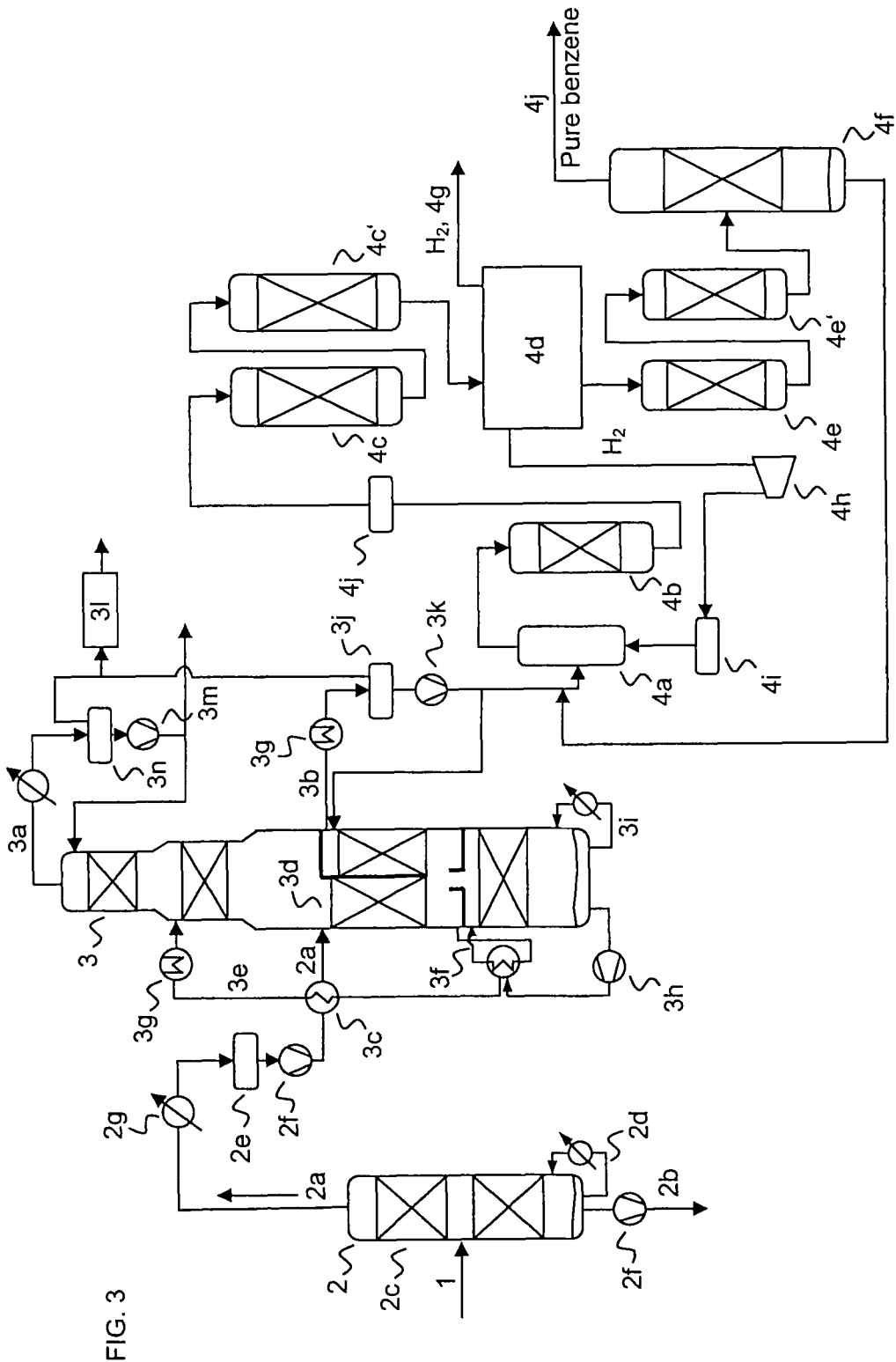
FIG. 3 shows an embodiment of an apparatus for carrying out the present invention.

FIG. 3 shows an apparatus for carrying out the process according to the invention. The aromatics-containing starting gasoline (1) is fed to a distilling column (2) where the starting gasoline is fractionated into a lower boiling (2a) and a higher boiling (2b) aromatics fraction each containing non-aromatic compounds. These fractions may, for example, mainly contain benzene (2a) or mainly toluene and xylenes (2b). The higher boiling fraction (2b) can be withdrawn. These fractions typically also contain olefins. Depending on the composition of the starting gasoline it is also be possible to use two distilling columns. The separation is performed in a pre-distilling column (2) with special devices (2c) allowing an enhanced separation of the mixture. In this drawing the distillation is also provided with apparatuses (2d) that serve to maintain the temperature required for the distillation, so-called reboilers. Also provided are intermediate vessels (2e), compressors (2f) and intermediate heaters (2g). The two fractions are then fed at two different feed points to the distilling column provided for the extractive distillation (3). The lower boiling aromatics fraction (2a) is adjusted to the temperature and pressure level required for the extractive distillation by means of intermediate heaters (2g), compressors (2f) and heat exchangers (3c). In this column for the extractive distillation (3) the aromatics mixture is fractionated into an aromatics-lean (3a) and an aromatics-rich (3b) hydrocarbon mixture, the aromatics-lean hydrocarbon fraction (3a) being obtained at the head of the column and the aromatics-containing hydrocarbon fraction which is not lean in aromatics can be withdrawn in the form of an aromatics concentrate (3b) from a lateral outlet of the column. The starting mixture (2a) is fed from a special distilling column with two compartments (3d) located in the main column section and provided with internals which serve to enhance the mass transfer. The special design of the column permits circulation of the extracting solvent in a loop (3e) and to occasionally refill solvent that has decomposed or escaped. The column houses heat exchangers (3c, 3f, 3g) to maintain the temperature of the extracting solvent at a level required for the extractive distillation. In addition, the column also houses devices which keep the whole material flow at a pressure and a temperature required for the extractive distillation, for example, a compressor (3h) and a reboiler (3i). An intermediate vessel (3j) and a compressor (3k) serve to provide the aromatics concentrate. The aromatics-lean hydrocarbon fraction (3a) contains olefins, diolefins and triolefins beside the paraffins and is withdrawn via a collecting tank (3l). At the head of the column, there is a vacuum pump (3m) to maintain the vacuum and an intermediate vessel (3n).

The aromatics concentrate (3b) is then transferred to the unit for hydrodealkylation. According to the embodiment shown here, this unit includes an evaporator (4a), a pre-treatment reactor (4b), two dealkylation reactors (4c,4c'), a hydrogen separator (4d), two post-treatment columns for purification (4e,4e') and a distilling column (4f). The aromatics-containing concentrate is first introduced into the evaporator (4a) and then passed to the pre-treatment reactor (4b) in vaporous form. Here, possible remainders of olefins or diolefins are hydrogenated. After this pre-treatment, the aromatics-containing mixture is transferred to the dealkylation reactors (4c,4c') of which two are provided here. These normally consist of tubes provided for the passage of dealkylated aromatics concentrate which are fired by burners. In this way, vaporous aromatics and alkanes are produced from the alkyl chains which—under the conditions applied—are normally converted into methane. The gas mixture obtained is routed to a hydrogen separator (4d) which removes the hydrogen and either withdraws it with the methane (4g) or recycles it into the evaporator (4a) via a compressor (4h) and an intermediate vessel (4i). The aromatics mixture from the hydrogen separator (4d) is routed to packed-bed columns (4e,4e') which are packed with clay material according to a typical embodiment. Here, for example, polymerisation products of the dealkylation reaction are separated. After this purification benzene is obtained which is very pure and can be further purified by distillation in a distilling column (4f). The pure benzene (4j) is discharged at the head of the column. Depending on the conditions of the dealkylation it is also possible to obtain higher alkylated products such as toluene or xylenes.

LIST OF REFERENCE NUMBERS AND DESIGNATIONS

1 Starting gasoline
2 Distilling column
2a Lower boiling aromatics fraction
2b Higher boiling aromatics fraction
2c Devices for enhancing the separation
2d Reboiler
2e Intermediate vessel
2f Compressor
2g Intermediate heater
3 Column for extractive distillation
3a Olefin-rich hydrocarbon mixture
3b Olefin-lean aromatics concentrate
3c Heat exchanger
3d Two compartment of the extractive distillation column
3e Extracting solvent circulated in a loop
3f, 3g Heat exchanger
3h Compressor
3i Reboiler
3j Intermediate vessel
3k Compressor
3l Collecting tank
3m Vacuum pump
3n Intermediate vessel
4a Evaporator
4b Pre-treatment reactor
4c,4c' Dealkylation reactor
4d Hydrogen separator
4e,4e' Post-treatment columns
4f Distilling column
4g Withdrawal of methane and hydrogen
4h Compressor
4i Intermediate vessel
4j Pure benzene discharge

TABLE 1

|  | Aromatics-containing starting mixture | Aromatics concentrate |
|---|---|---|
| Benzene | 2.29 | none |
| Toluene | 71.67 | 85.07 |
| $C_8$ aromatics (ethyl benzene and xylenes) | 11.79 | 14.14 |
| $C_9$ aromatics | 0.20 | 0.37 |
| n-heptane | 1.75 | none |
| iso-heptanes | 0.07 | none |
| $C_7$-naphthenes | 5.57 | none |
| n-octane | 0.88 | none |
| iso-octanes | 2.88 | <0.01 |
| $C_8$-naphthenes | 1.49 | <0.01 |
| n-nonane | 0.05 | 0.11 |
| iso-nonane | 0.44 | 0.08 |
| $C_9$-naphthenes | 0.60 | 0.09 |
| n-decane | none | none |
| iso-decan | 0.07 | 0.08 |
| $C_{10}$-naphthenes | none | none |
| Other | remainder to 100 | remainder to 100 |
| Total of aromatics | 85.99 | 99.56 |
| Total of (n + i)-paraffins | 6.01 | 0.15 |
| Total of naphthenes | 7.63 | 0.05 |

The invention claimed is:

1. A process for the dealkylation of a hydrocarbon mixture rich in $C_7$ to $C_9$ aromatics, comprising:
submitting the aromatics-rich starting hydrocarbon mixture to an extractive distillation in which the aromatics-containing hydrocarbon mixture is distilled by means of a suitable extracting solvent and freed from it, obtaining a product flow significantly depleted from aromatic hydrocarbons and free of solvent as well as an aromatics concentrate significantly enriched in aromatic hydrocarbons and free of solvent;
passing the solvent-free aromatics concentrate to a reactor for hydrodealkylation after the extractive distillation, where it is reacted with hydrogen, giving a dealkylated aromatics stream as main product and a paraffinic hydrocarbon stream and a methane stream as by-products; and
passing the aromatic hydrocarbon stream to a purification unit for treatment; wherein
the extractive distillation and recovery of the extracting solvent take place in one column.

2. The process according to claim 1, wherein the purification unit is a fractional distillation stage.

3. The process according to claim 1, wherein the purification unit is a flash distillation stage.

4. The process for the dealkylation of a hydrocarbon mixture rich in aromatics according to claim 1, wherein the aromatics-containing starting mixture is fully hydrogenated pyrolysis gasoline.

5. The process for the dealkylation of a hydrocarbon mixture rich in aromatics according to claim 1, wherein the aromatics-containing starting mixture is catalytically reformed gasoline.

6. The process for the dealkylation of a hydrocarbon mixture rich in aromatics according to claim 1, wherein the aromatics-containing starting mixture is coke-oven light oil refined under pressure.

7. The process for the dealkylation of a hydrocarbon mixture rich in aromatics according to claim 1, wherein the process produces a dealkylated and purified aromatics stream which is pure benzene.

8. The process for the dealkylation of a hydrocarbon mixture rich in aromatics according to claim 1, wherein the aromatics-containing starting mixture is submitted to a fractional distillation in a distilling column before being passed to the extractive distillation.

9. The process for the dealkylation of a hydrocarbon mixture rich in aromatics according to claim 1, wherein the aromatics-containing starting mixture is brought into contact with water, an acid, a suitable solvent or with a mixture of these substances before being passed to the extractive distillation.

10. The process for the dealkylation of a hydrocarbon mixture rich in aromatics according to claim 1, wherein the aromatics-containing starting mixture is submitted to a hydrogenation before being passed to the extractive distillation.

11. The process for the dealkylation of a hydrocarbon mixture rich in aromatics according to claim 1, wherein a hydrogenation is carried out between the process steps of extractive distillation and hydrodealkylation.

12. The process for the dealkylation of a hydrocarbon mixture rich in aromatics according to claim 1, wherein the extracting solvent is an N-substituted solvent with 1 to 8 carbon atoms in the substituent.

13. The process for the dealkylation of a hydrocarbon mixture rich in aromatics according to claim 1, wherein the extracting solvent is N-formyl morpholine.

14. The process for the dealkylation of a hydrocarbon mixture rich in aromatics according to claim 1, wherein the extracting solvent for the extractive distillation is N-methylpyrrolidone, sulfolane, methyl sulfonale, an alkylene glycol or an alkylated alkylene glycol or a mixture of these substances.

15. The process for the dealkylation of a hydrocarbon mixture rich in aromatics according to one of claim 12, wherein an extracting solvent mixture used for the extractive distillation contains water.

16. The process for the dealkylation of a hydrocarbon mixture rich in aromatics according to claim 1, wherein the hydrogenation step for hydrodealkylation is a thermal process.

17. The process for the dealkylation of a hydrocarbon mixture rich in aromatics according to claim 1, wherein the hydrogenation step for hydrodealkylation is a catalytic process.

18. A process for the dealkylation of a hydrocarbon mixture rich in $C_7$ to $C_9$ aromatics, comprising:

submitting the $C_7$ to $C_9$ aromatics-rich starting hydrocarbon mixture to an extractive distillation in which the aromatics-containing hydrocarbon mixture is distilled by means of a suitable extracting solvent and freed from it, obtaining a product flow significantly depleted from aromatic hydrocarbons and free of solvent as well as an aromatics concentrate significantly enriched in aromatic hydrocarbons and free of solvent, which concentrate comprises $C_7$ to $C_9$ aromatics;

passing the solvent-free aromatics concentrate to a reactor for hydrodealkylation after the extractive distillation, where it is reacted with hydrogen, giving a dealkylated aromatics stream as main product and a paraffinic hydrocarbon stream and a methane stream as by-products; and passing the aromatic hydrocarbon stream to a purification unit for treatment; wherein the extractive distillation and recovery of the extracting solvent take place in one column.

\* \* \* \* \*